US012758741B2

(12) United States Patent
Motose et al.

(10) Patent No.: US 12,758,741 B2
(45) Date of Patent: Oct. 13, 2026

(54) CATHETER HAVING SHAFT ACCOMMODATION PORTION THAT ACCOMMODATES AND IS FUSED TO ELONGATED SHAFT

(71) Applicant: TERUMO KABUSHIKI KAISHA, Tokyo (JP)

(72) Inventors: Yuji Motose, Kanagawa (JP); Daisuke Shimada, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1053 days.

(21) Appl. No.: 17/893,799

(22) Filed: Aug. 23, 2022

(65) Prior Publication Data

US 2022/0401695 A1 Dec. 22, 2022

Related U.S. Application Data

(63) Continuation of application No. PCT/JP2021/008615, filed on Mar. 5, 2021.

(30) Foreign Application Priority Data

Mar. 5, 2020 (JP) ................................ 2020-038156

(51) Int. Cl.
*A61M 25/00* (2006.01)

(52) U.S. Cl.
CPC .... *A61M 25/0097* (2013.01); *A61M 25/0014* (2013.01); *A61M 25/0045* (2013.01)

(58) Field of Classification Search
CPC .......... A61M 25/0097; A61M 25/0014; A61M 2025/0098; A61M 25/0625; A61M 39/02; A61M 5/3275; A61M 5/3293
See application file for complete search history.

(56) References Cited

U.S. PATENT DOCUMENTS

| | | | | |
|---|---|---|---|---|
| 3,720,210 A | 3/1973 | Diettrich | | |
| 3,802,433 A * | 4/1974 | Raven | A61M 25/0014 | 604/533 |
| 4,191,185 A * | 3/1980 | Lemieux | A61M 25/0014 | 604/533 |
| 4,231,367 A * | 11/1980 | Rash | A61M 25/0014 | 604/165.02 |

(Continued)

FOREIGN PATENT DOCUMENTS

| | | |
|---|---|---|
| CN | 106798961 A | 6/2017 |
| DE | 3045453 A1 | 6/1982 |

(Continued)

OTHER PUBLICATIONS

International Search Report (PCT/ISA/210) with translation and Written Opinion (PCT/ISA/237) mailed on Apr. 6, 2021, by the Japan Patent Office as the International Searching Authority for International Application No. PCT/JP2021/008615. (8 pages).

(Continued)

*Primary Examiner* — Theodore J Stigell
*Assistant Examiner* — Benjamin Koo
(74) *Attorney, Agent, or Firm* — BUCHANAN INGERSOLL & ROONEY PC

(57) ABSTRACT

A catheter is configured to reduce a possibility that a shaft of a catheter inserted into a body comes off from a hub on a proximal side when a contrast agent is injected at a high pressure and the shaft is pulled out. The catheter includes a shaft and a hub that are directly fusion-bonded at a shaft accommodation portion of the hub that accommodates a proximal end of the shaft and a vicinity of the proximal end and a minimum inner diameter of the shaft accommodation portion is at any portion of the fusion surface. The shaft is thus prevented from coming off from the hub, safety of a worker is achieved without using an adhesive, a yield is further improved, and a manufacturing cost and a cost required for ensuring safety are reduced.

20 Claims, 2 Drawing Sheets

(56) References Cited

U.S. PATENT DOCUMENTS

| | | | | |
|---|---|---|---|---|
| 4,409,046 | A | 10/1983 | Holzwarth et al. | |
| 4,806,182 | A * | 2/1989 | Rydell | B29C 66/71 156/303.1 |
| 5,030,205 | A * | 7/1991 | Holdaway | A61M 25/0014 604/239 |
| 2015/0127043 | A1 * | 5/2015 | Cope | A61M 25/1038 606/194 |
| 2016/0206858 | A1 * | 7/2016 | Ishida | A61M 25/0108 |
| 2017/0119997 | A1 * | 5/2017 | Burkholz | A61M 39/10 |
| 2017/0151417 | A1 | 6/2017 | Takemura et al. | |
| 2018/0071485 | A1 * | 3/2018 | Gupta | A61M 25/0097 |
| 2019/0358433 | A1 * | 11/2019 | Yokota | A61M 25/0097 |
| 2020/0023101 | A1 * | 1/2020 | Oiwa | A61L 29/106 |

FOREIGN PATENT DOCUMENTS

| | | | | |
|---|---|---|---|---|
| EP | 0 109 657 | A1 | 5/1984 | |
| EP | 1 466 644 | A2 | 10/2004 | |
| JP | S6317486 | U | 5/1988 | |
| JP | H10180802 | A | 7/1998 | |
| WO | 2014103599 | A1 | 7/2014 | |
| WO | 2016092208 | A1 | 6/2016 | |
| WO | WO-2018181184 | A1 * | 10/2018 | A61L 31/16 |
| WO | 2018207758 | A1 | 11/2018 | |

OTHER PUBLICATIONS

The extended European Search Report issued Jul. 31, 2023, by the European Patent Office in corresponding European Patent Application No. 21763772.7-1122. (8 pages).

The First Office Action issued on May 18, 2025, by the State Intellectual Property Office of the People's Republic of China in Chinese Patent Application No. 202180005930.4 and an English translation of the Action. (13 pages).

* cited by examiner

CATHETER HAVING SHAFT ACCOMMODATION PORTION THAT ACCOMMODATES AND IS FUSED TO ELONGATED SHAFT

CROSS-REFERENCES TO RELATED APPLICATIONS

This application is a continuation of International Application No. PCT/JP2021/008615 filed on Mar. 5, 2021, which claims priority to Japanese Patent Application No. 2020-038156 filed on Mar. 5, 2020, the entire content of both of which is incorporated herein by reference.

TECHNOLOGICAL FIELD

This invention generally relates to a catheter and a catheter manufacturing method.

BACKGROUND DISCUSSION

In general, a catheter includes a shaft having a lumen extending from a distal end to a proximal end, and a hub disposed at the proximal end of the shaft and communicating with the lumen in order to be connected to a syringe or the like.

As a method for fixing the proximal end of the shaft to the hub, an insert molding method, an adhesion method using an adhesive, a fusion method using a laser, and the like are known.

SUMMARY

In an insert molding method disclosed in Japanese Patent Application Publication No. 10-180802 (JP-A-H10-180802), the shaft is disposed in an injection mold, a part of the shaft is pressed by a fixing pin, and a resin for the hub is injection-molded at a high temperature and a high pressure. Therefore, unlike a metal needle or the like, when a resin catheter is molded, deformation of the shaft caused by the fixing pin or displacement of the shaft in a longitudinal axis direction may occur.

In a case where an adhesive is used as in Japanese Utility Model Publication No. 63-17486 (JP-UM-B-S63-17486), when a gap between an outer diameter of the shaft and a lumen of a shaft accommodation portion of the hub is too small, the adhesive does not flow around, and a gap remains between the hub and the shaft, so that a contrast agent may leak at the time of injection of the contrast agent. On the other hand, when the gap is too large, the adhesive may flow into the lumen and the lumen may be narrowed.

In particular, in a support catheter that supports a guidewire in a blood vessel, a difference between an inner diameter of a shaft and an outer diameter of the guidewire passing through a lumen of the shaft is small, so that it is difficult to insert the guidewire into the lumen when the lumen is narrow.

In addition, when adhesive is used, protective tools such as goggles and gloves are required, which imposes a burden on a worker who wears the protection tools.

In addition, when the shaft and the hub are fused by an infrared laser in International Patent Application Publication No. 2016/092208 (WO2016/092208), since content of a pigment is extremely high at 10 wt % or more and two or more kinds of pigments are used, a color of the shaft cannot be freely selected.

(1) The catheter disclosed here includes: a shaft having a lumen communicating from a distal end to a proximal end and a shaft outer surface extending along a shaft long axis; and a hub attached to the proximal end of the shaft. The hub has a hub distal opening on a distal side, a shaft accommodation portion holding the shaft, and a hub proximal opening, the shaft accommodation portion has an adjacent surface, formed at a proximal end thereof, adjacent to a shaft proximal surface of the shaft, the adjacent surface has a hole communicating with the hub proximal opening and close to the shaft proximal opening, a fusion surface is formed by directly fusion-bonding a proximal side of the shaft outer surface on the proximal side and the hub along the shaft long axis, an inner diameter of the hub distal opening is larger than a diameter of the adjacent surface and the shaft accommodation portion has a smallest inner diameter at the fusion surface.

(2) In the catheter according to (1), the smallest inner diameter of the shaft accommodation portion at the fusion surface may be smaller than an outer diameter of the shaft proximal surface.

(3) In the catheter according to (1), a gap may exist between the shaft accommodation portion and a shaft proximal end vicinity outer surface on a proximal side of the fusion surface.

According to another aspect, a catheter comprises: an elongated shaft having a longitudinal extent extending from a distal end of the elongated shaft to a proximal end of the elongated shaft, and a hub that includes a shaft accommodation portion in which is accommodated a proximal portion of the elongated shaft. The elongated shaft includes a lumen extending along the longitudinal extent of the elongated shaft and opening to the proximal end of the shaft at a shaft proximal opening while also opening to the distal end of the shaft. The elongated shaft includes a shaft proximal end surface at the proximal end of the elongated shaft, and the elongated shaft also includes a shaft outer surface extending along the longitudinal extent of the elongated shaft. The shaft accommodation portion of the hub possesses an inner diameter, and the hub also includes a hub lumen extending from a hub proximal opening at a proximal end of the hub toward a distal end of the hub, with the hub lumen communicating with the shaft accommodation portion. The hub also includes a hub distal opening at the distal end of the hub that communicates with the shaft accommodation portion of the hub. The shaft outer surface of the proximal portion of the elongated shaft and an inner surface of the shaft accommodation portion are directly fusion-bonded to each other along a portion of the longitudinal extent of the elongated shaft, without an adhesive interposed between the elongated shaft and the hub, to form a longitudinally extending fusion surface. The proximal portion of the shaft accommodation portion of the hub includes an adjacent surface that faces toward the shaft proximal end surface of the elongated shaft, and the fusion surface possesses an inner diameter that is a smaller than the inner diameter of all other portions of the shaft accommodation portion of the hub positioned proximally and distally of the fusion surface.

In the catheter according to this invention, the shaft outer surface and the hub are directly fusion-bonded without an adhesive interposed between the shaft and the hub, and the inner diameter of the fusion surface is the smallest between a distal opening of the shaft accommodation portion and the adjacent surface on the proximal side, so that the shaft is firmly coupled to the hub, and the shaft is prevented from coming off from the hub when a high pressure is applied at the time of injection of a contrast agent or when the shaft is pulled out from a body.

Further, a manufacturing cost can be reduced since a positional deviation defect at the time of insert molding is less likely to occur and a large number of protective tools and exhaust ducts for protecting a worker in order to achieve safety of the worker and increase production are not required due to that it is not necessary to use an adhesive for the coupling between the hub and the shaft, that is, conflicting problems that are a reduction in manufacturing cost and a reduction in safety cost can be solved at the same time.

DETAILED DESCRIPTION

Set forth below with reference to the accompanying drawings is a detailed description of an embodiment of a catheter representing an example of the new catheter disclosed here. The dimensions or scales on the drawings may be exaggerated or different from actuality/reality for convenience of description and illustration.

Figure 1:
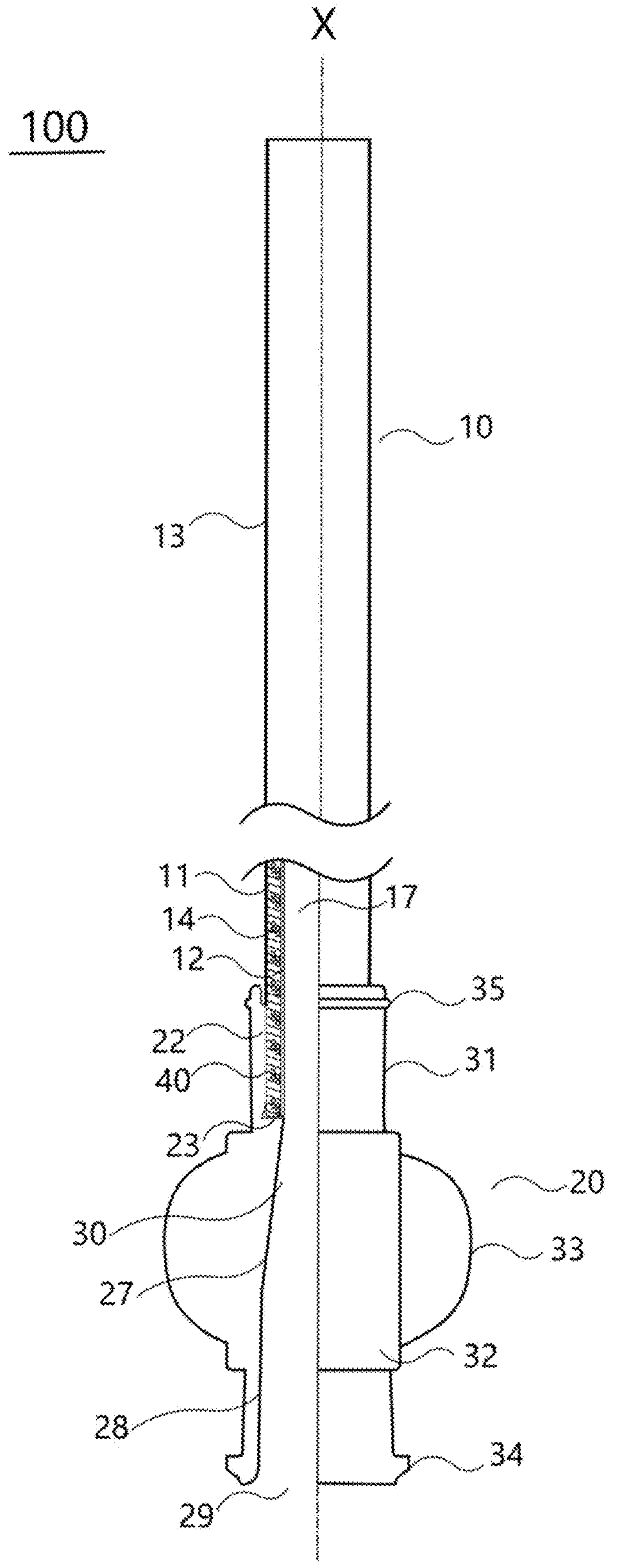
FIG. 1 is a plan view showing a partial cross-section of a catheter according to one example disclosed here.

A catheter 100 according to this disclosure includes a shaft 10 and a hub 20 as shown in FIG. 1. In addition to a catheter supporting a guidewire, the catheter may be a guiding catheter, an angiographic catheter, or a microcatheter, or may be a balloon catheter or an imaging catheter having a lumen for inflating.

In addition, the catheter may be an over-the-wire (OTW) type catheter in which the shaft and the hub communicate from a distal end to a proximal end, or may be a type of catheter having a lumen in which a guidewire lumen at the distal end of the catheter is opened in the middle of the shaft and communicates from a balloon at the distal portion to the hub at the proximal end of the catheter, such as a rapid exchange (RX) balloon catheter.

The shaft (elongated shaft) 10 has a lumen 17 that extends along the shaft 10 from a distal end to a proximal end, and an outer surface 13 extending from the distal end to the proximal end.

Figure 2:
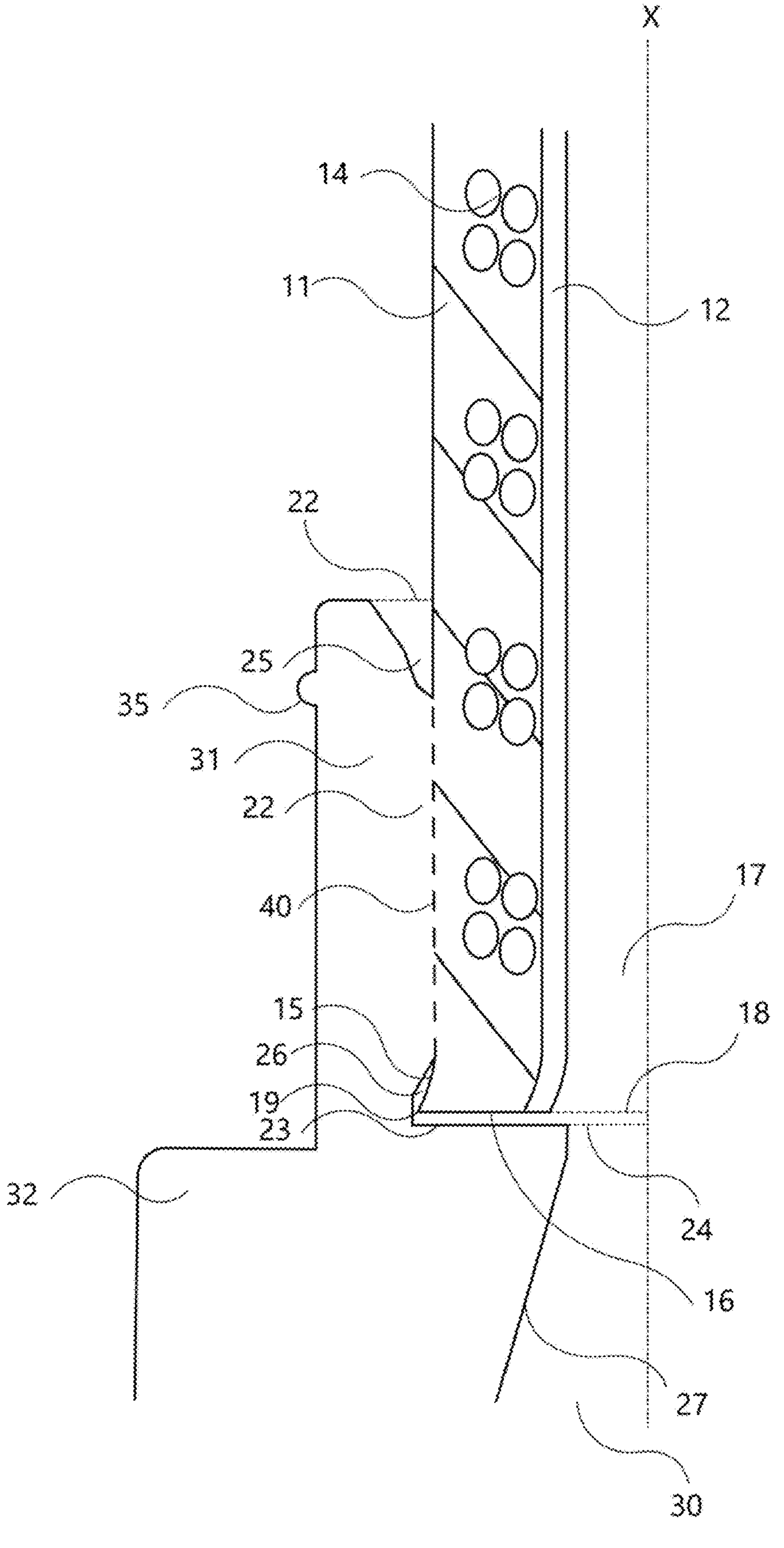
FIG. 2 is an enlarged vertical cross-sectional view taken along a longitudinal axis X of a hub and a shaft proximal portion.

As shown in FIG. 2, the shaft 10 has, on a proximal side or a proximal end of the shaft 10, a shaft proximal surface (shaft proximal end surface) 16 formed by cutting the proximal end of the shaft 10 perpendicularly to a shaft longitudinal axis X, and has a shaft proximal opening 18 which is a proximal end of the lumen in the shaft.

The shaft outer surface 13 has a shaft proximal end vicinity outer surface 15 extending from the proximal end of the shaft toward the distal end of the shaft, and a fusion surface 40 fusion-bonded with the hub, and the shaft outer surface 13 is accommodated in a shaft accommodation portion 22 from a distal end portion of the fusion surface 40 to the shaft proximal opening 18.

As shown in FIGS. 1 and 2, the hub 20 has a hub lumen 30 that extends along the hub 20 from a proximal end of the hub 20 to a distal end of the hub on an inner surface or interior of the hub 20. The hub lumen 30 has a hub distal opening 21 and the shaft accommodation portion 22 positioned in that order from a distal side (distal end), and further includes, at a proximal end of the shaft accommodation portion 22, an adjacent surface 23 that is adjacent to (faces toward) the shaft proximal surface 16. At a center of the adjacent surface 23, a hole 24 is formed at a position facing the shaft proximal opening 18 of the lumen 17. An inner diameter of the hub distal opening 21 is larger than a diameter of the adjacent surface 23. Therefore, the shaft 10 can be easily inserted into the shaft accommodation portion 22.

The hole 24 has a substantially circular shape around a longitudinal axis, or a substantially cylindrical shape or a substantially circular truncated cone shape having a length in a longitudinal axis direction. The hole 24 is coaxial with the shaft accommodation portion 22, and preferably is coaxial with the lumen 17. The inner diameter of the shaft 10 and the inner diameter of the hole 24 may preferably be the same.

A proximal end of the hole 24 communicates with a tapered portion 27 of the hub lumen that expands toward a proximal direction, a proximal end of the tapered portion 27 communicates with a hub proximal opening 29, and a part of the tapered portion 27 may be a luer tapered portion 28 that can be interlocked with a syringe (not shown).

Accordingly, a guidewire or a treatment catheter inserted from the hub proximal opening 29 can smoothly pass through the hub lumen 30, protrude from the catheter distal end through the shaft lumen 17, and easily reach a target position such as a lesion area.

An outer side of the hub 20 includes, in order from the distal side (distal end), a hub distal portion 31 including the shaft accommodation portion 22, a body portion 32 that can be gripped at the time of surgery and on which a display of a catheter size can be described, a wing 33, and a hub connector portion 34 that has a screw thread projection or the like that engages with a luer-lock type syringe or the like and has the hub proximal opening 29.

In addition, the hub distal portion 31 may be provided with a projection portion 35 fitted into a hole portion or a recess portion of an anti-kink protector (not shown).

Next, a method for fusing the shaft 10 and the hub 20 will be described. The proximal end of the shaft 10 is inserted into the shaft accommodation portion 22, and the shaft proximal surface 16 is brought close to the adjacent surface 23, but the shaft proximal surface 16 may be brought into contact with the adjacent surface 23, or an outer edge of the shaft proximal surface 16 may abut against (contact) an inner surface of the shaft accommodation portion 22 on a distal side of the adjacent surface 23 with a gap between the shaft proximal surface 16 and the adjacent surface 23.

A mandrel is then inserted into the lumen 17 of the shaft, and the shaft outer surface 13 and the shaft accommodation portion 22 of the hub 20 are heated so that the shaft outer surface 13 and the shaft accommodation portion 22 are melted to form the fusion surface 40.

A heating method is not particularly limited, and examples of the heating method include a method that involves emitting electromagnetic waves having a wavelength that can pass through the hub 20 but cannot pass through the shaft outer surface 13.

Since electromagnetic waves cannot pass through the shaft outer surface 13, the shaft outer surface 13 is first heated and melted, and the heat of the heated shaft outer surface 13 is transmitted to the shaft accommodation portion 22 to melt the shaft accommodation portion 22, thereby forming the fusion surface 40.

The electromagnetic waves include infrared rays in addition to heat, microwaves, and visible light. The infrared rays include near-infrared rays having a wavelength of about 0.7

μm to 2.5 μm, mid-infrared rays having a wavelength of about 2.5 μm to 4 μm, and far-infrared rays having a wavelength of about 4 μm to 1000 μm. The electromagnetic waves may include one or more kinds of the near-infrared rays, the mid-infrared rays, and the far-infrared rays, and may include visible light or microwaves.

A method for emitting the electromagnetic waves is not particularly limited, and a fiber laser, a semiconductor solid-state laser such as a YAG laser using neodymium, or the like may be used.

The expression that "the electromagnetic waves can pass through" means that an object appears to be transparent to the naked eye with respect to the visible light, and that a sheet having a thickness of 0.4 mm to 0.5 mm and produced by melting and pressing resin pellets has a transmittance (hereinafter, referred to as "transmittance") of 80% or more, preferably 85% or more with respect to a wave having a specific wavelength when being measured using a spectroscopic analyzer, for example, a Fourier transform infrared and near-infrared spectroscopic analyzer. Therefore, since the expression "the electromagnetic waves can pass through" is not limited to a case that an object is transparent with respect to the visible light, a case that an object is transparent with respect to a wave having a specific wavelength even if the object appears to be colored or opaque to the naked eye is included.

In addition, the expression that "the electromagnetic waves cannot pass through" means that an object appears to be opaque or colored to the naked eye with respect to visible light, and that an object has a transmittance of less than 80%, preferably less than 10%, still preferably less than 1%. Therefore, since the expression "the electromagnetic waves cannot pass through" is not limited to a case that an object is opaque or colored with respect to visible light, a case that an object is opaque with respect to a wave having a specific wavelength or absorbs the wave even if the object appears to be transparent to the naked eye is included.

The shaft 10 of the catheter 100 shown in FIG. 2 has an outer layer 11 and an inner layer 12, and a reinforcing wire 14 obtained by weaving a metal wire or the like is positioned between the inner layer 12 and the outer surface of the outer layer 11. In the outer layer 11, a pigment that does not transmit or absorbs heat or the electromagnetic waves may be mixed in an amount of 0.01 wt % or more and less than 10 wt %, preferably 0.05 wt % or more and 5 wt % or less, and still more preferably 0.1 wt % or more and 1 wt % or less of a total of a resin of the outer layer 11.

Alternatively, a resin may be one that does not contain a pigment, a contrast agent, or the like and has a low transmittance with respect to a wave having a specific wavelength, or the pigment may be replaced with a radiopaque metal or mixture of the pigment and the radiopaque metal.

The pigment is not particularly limited as long as the pigment is a pigment that develops (i.e., is visually seen as or recognized as) white, black, blue, red, or yellow, or a mixture thereof. A black pigment is preferable as the pigment that easily absorbs the electromagnetic waves, and the black pigment may be, for example, carbon black. The radiopaque materials may be, for example, a compound of gold, bismuth, or tungsten, and radiopaque materials in a powder form are more preferable.

Alternatively, the outer layer may be one that has a low transmittance with respect to a wave having a specific wavelength even if the outer layer is transparent to the naked eye.

Examples of the resin of the outer layer 11 include, in addition to a polyamide resin, a polyester resin, a polyolefin resin, and a polyurethane resin, a polyamide elastomer, a polyester elastomer, a polyurethane elastomer, or a mixture of one or more of these resins or elastomers, or a mixture of the resins or elastomers having different hardness. These elastomers having different hardness may be arranged such that the outer layer 11 is flexible from the proximal end toward the distal end.

A resin of the inner layer 12 may be the same as that of the outer layer 11, or may be a resin different from that of the outer layer 11, or may be a polytetrafluoroethylene resin in order to improve sliding property of the inner surface.

The material from which the hub 20 is fabricated is not particularly limited as long as the hub 20 is made of a thermoplastic resin that can be injection-molded. Preferably, the thermoplastic resin should be able to easily transmit the heat or the electromagnetic waves. Specific examples of the thermoplastic resin include a polyolefin resin, a polyamide resin, a polycarbonate resin, and a polyester resin.

For example, when the shaft 10 and the hub 20 are fused by being irradiated with an infrared laser, electromagnetic waves transmitted through the hub 20, which is transparent with respect to a wave having a wavelength of the irradiated infrared laser, are absorbed by the opaque resin, pigment, or the like of the outer layer 11 of the shaft 10 to mainly generate heat, the resin of the outer layer 11 of the shaft is melted, the heat from the outer layer is transferred to the shaft accommodation portion 22 of the hub 20, and at least a part of an inner surface of the shaft accommodation portion 22 is melted. When the inner surface of the shaft accommodation portion 22 is melted, an inner diameter of the shaft accommodation portion 22 is reduced, the shaft accommodation portion 22 is brought into contact with the shaft outer surface 13, and the fusion surface 40 is formed.

Accordingly, since the inner diameter of the shaft accommodation portion 22 is the smallest at the fusion surface 40, the shaft 10 is less likely to come off from or be separated from the hub 20. That is, the inner diameter of the fusion surface 40 is smaller than the inner diameter of all other portions of the shaft accommodation portion 22 of the hub 10 positioned proximally and distally of the fusion surface 40.

The inner diameter d of the shaft accommodation portion 22 at the fusion surface 40 is smaller than the inner diameter D of the adjacent surface 23. The inner diameter d of the shaft accommodation portion 22 at the fusion surface 40 being smaller than the inner diameter D of the adjacent surface 23 means that, for example, the inner diameter d at the fusion surface 40 is smaller than the inner diameter D of the adjacent surface 23 when the inner diameter at the fusion surface 40 and the inner diameter of the hub lumen 30 at the adjacent surface 23 are compared in a cross-section perpendicular to the shaft longitudinal axis X.

A difference between the inner diameter d of the shaft accommodation portion 22 at the fusion surface 40 and the inner diameter D of the adjacent surface 23 is 0 mm or more and 0.5 mm or less, preferably more than 0 mm and 0.2 mm or less. Since the shaft proximal surface 16 can be inserted into the shaft accommodation portion 22 only on a distal side of the adjacent surface 23 when the difference is less than 0 mm, a gap is generated between the shaft proximal surface 16 and the adjacent surface 23.

When the difference between the inner diameter of the shaft accommodation portion 22 at the fusion surface 40 and the inner diameter of the adjacent surface 23 is more than 0.5 mm, the fusion surface 40 between the shaft 10 and the hub 20 may be not sufficiently formed and tensile strength may be reduced.

In addition, a distal gap 25 may be formed between the hub distal opening 21 and the fusion surface 40 on the distal side. The distal gap 25, which may extend over a distal end portion of the hub, may be defined as a difference between an outer diameter of the shaft 10 and the inner diameter of the hub accommodation portion 22 that changes along the shaft longitudinal axis X, or may be defined as a difference between the outer diameter of the shaft 10 and an inner diameter of the distal gap 25 on a proximal side of the hub distal opening 21. As shown in FIG. 2, the distal gap 25 may be configured so that the inner surface of the hub 10 in the distal end portion of the hub 10 is spaced at a differing distances from the shaft outer surface 13 along the shaft longitudinal axis X so that the size (radial dimension) of the distal gap 25 narrows or becomes smaller in the proximal direction.

The difference between the outer diameter of the shaft and the inner diameter of the shaft accommodation portion 22 at the distal gap 25 may be a gap through which the shaft 10 can be inserted into the shaft accommodation portion 22, and may be more than 0 mm and 0.2 mm or less.

An inner diameter of the shaft proximal opening 18 may be larger than the inner diameter of the hole 24 (as shown in FIG. 2) to form a flare portion 19, and a mandrel may be inserted into the lumen 17 to enlarge a diameter of the shaft proximal surface 16 so that a guidewire does not become hooked on the shaft proximal opening 18 when the guidewire is inserted.

Accordingly, since the inner diameter of the shaft accommodation portion 22 at the fusion surface 40 is smaller than an outer diameter of the flare portion 19 that is the shaft proximal surface 16, the shaft 10 can be prevented from coming off from the hub 20.

In addition, a proximal gap 26 may be formed between the shaft proximal end vicinity outer surface 15 and the shaft accommodation portion (inner surface of the shaft accommodation portion) 22 in accordance with a gap between the shaft proximal surface 16 and the adjacent surface 23.

Processing time can be shortened by shortening the fusion surface 40.

Accordingly, the shaft 10 is prevented from being pulled out from the hub 20 when a high pressure is applied at the time of injecting, in order to observe a state of a treatment site, an X-ray contrast agent by a contrast agent injection device connected to the luer tapered portion 28, or when the hub 20 is pulled at the time of pulling the shaft 10 inserted into the body out of the body after treatment is performed using the catheter 100.

The detailed description above describes embodiments of a catheter and a catheter manufacturing method representing examples of the new catheter and catheter manufacturing method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST

10 shaft
11 outer layer
12 inner layer
13 shaft outer surface
14 reinforcing wire
15 shaft proximal end vicinity outer surface
16 shaft proximal surface
17 lumen
18 shaft proximal opening
19 flare portion
20 hub
21 hub distal opening
22 shaft accommodation portion
23 adjacent surface
24 hole
25 distal gap
26 proximal gap
27 tapered portion
28 luer tapered portion
29 hub proximal opening
31 hub distal portion
32 hub body portion
33 wing
34 hub connector portion
5 projection portion
40 fusion surface
X shaft long axis

What is claimed is:

1. A catheter comprising:

a shaft that possesses a shaft longitudinal axis, the shaft also possessing a distal end and a proximal end, the shaft having a lumen extending from the distal end of the shaft to the proximal end of the shaft, the shaft including a shaft proximal end surface and a shaft proximal opening that is a proximal end of the lumen in the shaft, and the shaft also including a radially outwardly facing shaft outer surface extending continuously along the shaft in a proximal direction from the distal end of the shaft and terminating at the shaft proximal end surface, the shaft also including a radially inwardly facing shaft inner surface extending continuously along the shaft from the distal end of the shaft to the proximal end of the shaft, an entirety of the shaft outer surface being radially outwardly of the shaft inner surface;

a hub attached to the proximal end of the shaft, the hub including a distal end and a proximal end;

the hub including a hub distal opening at the distal end of the hub, a shaft accommodation portion in which is accommodated the proximal end of the shaft, and a hub proximal opening at the proximal end of the hub, the shaft accommodation portion extending from a proximal end of the shaft accommodation portion to a distal end of the shaft accommodation portion;

the shaft accommodation portion of the hub including an adjacent surface at the proximal end of the shaft accommodation portion, the adjacent surface of the shaft accommodation portion being positioned adjacent the shaft proximal end surface of the shaft;

the shaft accommodation portion having an inner surface that extends from the distal end of the shaft accommodation portion to the proximal end of the shaft accommodation portion and that terminates at the adjacent surface of the shaft accommodation portion;

the adjacent surface of the shaft accommodation portion including a hole that communicates with the hub proximal opening and that is positioned adjacent the shaft proximal opening;

a proximal portion of the shaft outer surface being directly fusion-bonded to the hub along the shaft longitudinal axis to form a fusion surface that extends along the shaft longitudinal axis, the radially outwardly facing shaft outer surface of a part of the proximal end of the shaft that is accommodated in the shaft accommodation portion of the hub being spaced from the inner surface of the shaft accommodation portion so that a gap exists between the shaft outer surface of the part of the proximal end the shaft and the inner surface of the shaft accommodation portion;

the gap being located, in a direction of the shaft longitudinal axis, between the fusion surface and the shaft proximal end surface of the shaft;

an inner diameter of the hub distal opening being larger than an inner diameter of the adjacent surface of the shaft accommodation portion, an inner diameter of the shaft accommodation portion, between the proximal end of the shaft accommodation portion and the distal end of the shaft accommodation portion, being smallest at the fusion surface.

2. The catheter according to claim 1, wherein the inner diameter of the shaft accommodation portion at the fusion surface is smaller than an outer diameter of the shaft proximal end surface.

3. The catheter according to claim 1, wherein the hub includes a distal end portion that extends proximally from the hub distal opening, an inner surface of the hub in the distal end portion of the hub facing the shaft outer surface and being spaced from the shaft outer surface.

4. The catheter according to claim 3, wherein the inner surface of the hub in the distal end portion of the hub is spaced at a differing distance from the shaft outer surface along the shaft longitudinal axis.

5. The catheter according to claim 1, wherein the lumen in the shaft is widened at a proximal end portion of the shaft so that an inner diameter of the lumen in the shaft at the shaft proximal end surface is larger than an inner diameter of the hole in the adjacent surface of the shaft accommodation portion.

6. The catheter according to claim 1, wherein the shaft outer surface of a proximal end portion of the shaft is outwardly flared so that an outer diameter of the proximal end portion of the shaft increases toward the shaft proximal end surface.

7. The catheter according to claim 1, wherein the shaft is made of a resin material and includes a reinforcing wire extending along the shaft.

8. The catheter according to claim 1, wherein the shaft is made of a resin material and includes a pigment that does not transmit or absorb heat or electromagnetic waves.

9. A catheter comprising:

an elongated shaft extending from a distal end of the elongated shaft to a proximal end of the elongated shaft so that the proximal end of the elongated shaft is on a proximal side of the distal end of the elongated shaft, the elongated shaft including a lumen extending along the elongated shaft and opening to the proximal end of the shaft at a shaft proximal opening while also opening to the distal end of the shaft, the elongated shaft including a shaft proximal end surface at the proximal end of the elongated shaft, the elongated shaft also including a shaft outer surface that faces radially outwardly, extends continuously in a proximal direction from the distal end of the elongated shaft to the proximal end of the elongated shaft and terminates at the shaft proximal end surface, the elongated shaft including a shaft inner surface that surrounds the lumen, extends continuously in the proximal direction from the distal end of the elongated shaft to the proximal end of the elongated shaft and terminates at the shaft proximal end surface, an entirety of the shaft inner surface being radially inwardly of the shaft outer surface;

a hub that includes a shaft accommodation portion in which is accommodated a proximal portion of the elongated shaft, the shaft accommodation portion possessing an inner diameter, the hub also including a hub lumen extending from a hub proximal opening at a proximal end of the hub toward a distal end of the hub, the hub lumen communicating with the shaft accommodation portion, the hub also including a hub distal opening at the distal end of the hub that communicates with the shaft accommodation portion of the hub;

the shaft outer surface of the proximal portion of the elongated shaft and an inner surface of the shaft accommodation portion being directly fusion-bonded to each other along a portion of the elongated shaft, without an adhesive interposed between the elongated shaft and the hub, to form a longitudinally extending fusion surface;

a proximal portion of the shaft accommodation portion of the hub including an adjacent surface that faces toward the shaft proximal end surface of the elongated shaft;

the radially outwardly facing shaft outer surface of the elongated shaft that extends continuously from the distal end of the elongated shaft to the proximal end of the elongated shaft including a portion that is spaced from the inner surface of the shaft accommodation portion so that a gap exists between the portion of the shaft outer surface of the elongated shaft and the inner surface of the shaft accommodation portion, the portion of the shaft outer surface of the elongated shaft being on the proximal side of the fusion surface; and the fusion surface possessing an inner diameter that is a smaller than the inner diameter of all other portions of the shaft accommodation portion of the hub positioned proximally and distally of the fusion surface.

10. The catheter according to claim 9, wherein the hub includes a distal end portion extending proximally from the hub distal opening, the distal end portion of the hub possessing an inner surface that faces the shaft outer surface of the elongated shaft and that is spaced from the shaft outer surface of the elongated shaft.

11. The catheter according to claim 9, wherein the hub includes a distal end portion extending proximally from the hub distal opening, the distal end portion of the hub possessing an inner surface that faces the shaft outer surface of the elongated shaft and that is spaced from the shaft outer surface so that a distal gap exists between the inner surface of the distal end portion of the hub and the shaft outer surface of the elongated shaft, a radial dimension of the distal gap varying along the elongated shaft.

12. The catheter according to claim 11, wherein the radial dimension of the distal gap at a distal part of the distal gap is larger than the radial dimension of the distal gap at a proximal part of the distal gap.

13. The catheter according to claim 9, wherein the lumen in the elongated shaft is expanded at a proximal end portion of the elongated shaft so that an inner diameter of the lumen in the elongated shaft at the shaft proximal end surface is larger than an inner diameter of the hub lumen at the adjacent surface of the shaft accommodation portion of the hub.

14. The catheter according to claim 9, wherein the shaft outer surface of a proximal end portion of the elongated shaft is outwardly flared so that an outer diameter of the proximal end portion of the elongated shaft increases toward the shaft proximal end surface.

15. The catheter according to claim 9, wherein a smallest inner diameter of the shaft accommodation portion at the fusion surface is smaller than an outer diameter of the shaft proximal end surface.

16. The catheter according to claim 9, wherein the elongated shaft is made of a resin material and includes a reinforcing wire extending along at least a portion of the elongated shaft.

17. The catheter according to claim 9, wherein the elongated shaft is made of a resin material and includes a pigment that does not transmit or absorb heat or electromagnetic waves.

18. A catheter comprising:

a shaft that is elongated and extends from a distal end of the shaft to a proximal end of the shaft, the shaft having a lumen extending throughout the shaft, the shaft having an inner surface that surrounds the lumen, that faces radially inwardly and that extends continuously in a proximal direction from the distal end of the shaft to the proximal end of the shaft;

the shaft including a shaft proximal end surface and a shaft proximal opening that is a proximal end of the lumen in the shaft, the shaft proximal end surface facing away from the distal end of the shaft, and the shaft also having a shaft outer surface extending continuously from the distal end of the shaft to the proximal end of the shaft, an entirety of the shaft outer surface being radially outwardly of the inner surface of the shaft;

a hub attached to the proximal end of the shaft, the hub including a distal end and a proximal end;

the hub including a hub distal opening at the distal end of the hub, a shaft accommodation portion in which is accommodated the proximal end of the shaft, and a hub proximal opening at the proximal end of the hub, the shaft accommodation portion extending from a proximal end of the shaft accommodation portion to a distal end of the shaft accommodation portion so that the proximal end of the shaft accommodation portion is on a proximal side of the distal end of the shaft accommodation portion and so that the distal end of the shaft accommodation portion is on a distal side of the proximal end of the shaft accommodation portion;

the shaft accommodation portion of the hub including an adjacent surface that is at the proximal end of the shaft accommodation portion and that faces towards the distal end of the hub, the adjacent surface of the shaft accommodation portion facing the shaft proximal end surface of the shaft, the shaft accommodation portion having a radially inwardly facing inner surface that extends continuously from the distal end of the shaft accommodation portion toward the proximal end of the shaft accommodation portion and that terminates at the adjacent surface of the shaft accommodation portion;

the adjacent surface of the shaft accommodation portion including a hole that communicates with the hub proximal opening and that is positioned adjacent the shaft proximal opening;

a proximal portion of the shaft outer surface being directly fusion-bonded to the hub along the shaft longitudinal axis to form a fusion surface that extends along the shaft longitudinal axis;

the radially inwardly facing inner surface of the shaft accommodation portion including a part located on the proximal side of the fusion surface, the radially outwardly facing shaft outer surface of the shaft that extends continuously from the distal end of the shaft to the proximal end of the shaft including a part located on the proximal side of the fusion surface;

the part of the radially inwardly facing inner surface of the shaft accommodation portion and the part of the radially outwardly facing shaft outer surface of the shaft facing one another and being spaced from one another so that a radial gap exists between the part of the radially inwardly facing inner surface of the shaft accommodation portion and the part of the radially outwardly facing shaft outer surface of the shaft, the radial gap being on the proximal side of the fusion surface and on the distal side of the adjacent surface of the shaft accommodation portion of the hub; and an inner diameter of the hub distal opening being larger than an inner diameter of the adjacent surface of the shaft accommodation portion, an inner diameter of the shaft accommodation portion being smallest, along its entire longitudinal extent, at the fusion surface.

19. The catheter according to claim 18, wherein the lumen in the shaft is expanded at a proximal end portion of the elongated shaft so that an inner diameter of the lumen in the shaft at the shaft proximal end surface is larger than an inner diameter of the hole of the adjacent surface of the shaft accommodation portion.

20. The catheter according to claim 19, wherein the adjacent surface of the shaft accommodation portion of the hub and the shaft proximal end surface of the shaft are axially spaced apart from one another so that an axial gap exists between the adjacent surface of the shaft accommodation portion of the hub and the shaft proximal end surface of the shaft.

* * * * *